(12) United States Patent
Li et al.

(10) Patent No.: US 8,916,736 B2
(45) Date of Patent: Dec. 23, 2014

(54) METHOD FOR SELECTIVE HYDROGENATION OF PHENYLACETYLENE USING COMPOSITE BED IN THE PRESENCE OF STYRENE

(75) Inventors: Siqin Li, Shanghai (CN); Juntao Liu, Shanghai (CN); Zhiyan Zhu, Shanghai (CN); Junhua Zhu, Shanghai (CN); Jun Kuai, Shanghai (CN)

(73) Assignees: Shanghai Research Institute of Petrochemical Technology, Sinopec, Shanghai (CN); China Petroleum & Chemical Corporation, Beijing (CN)

( * ) Notice: Subject to any disclaimer, the term of this patent is extended or adjusted under 35 U.S.C. 154(b) by 0 days.

(21) Appl. No.: 13/140,645

(22) PCT Filed: Dec. 17, 2009

(86) PCT No.: PCT/CN2009/001487
§ 371 (c)(1),
(2), (4) Date: Sep. 6, 2011

(87) PCT Pub. No.: WO2010/069145
PCT Pub. Date: Jun. 24, 2010

(65) Prior Publication Data
US 2011/0319684 A1      Dec. 29, 2011

(30) Foreign Application Priority Data
Dec. 18, 2008   (CN) .......................... 2008 1 0044147

(51) Int. Cl.
*C07C 5/11*         (2006.01)
*C07C 7/167*        (2006.01)
(52) U.S. Cl.
CPC ..................................... *C07C 7/167* (2013.01)
USPC ........... 585/270; 585/274; 585/273; 585/269; 585/265; 585/266
(58) Field of Classification Search
USPC .................. 585/250–277; 208/141, 142–145; 502/152–157, 161, 174, 180–185
See application file for complete search history.

(56) References Cited

U.S. PATENT DOCUMENTS

| | | | |
|---|---|---|---|
| 4,508,836 A | 4/1985 | Haag et al. | |
| 5,156,816 A | 10/1992 | Butler et al. | |
| 6,555,073 B1 | 4/2003 | Butler et al. | |
| 6,635,791 B1 | 10/2003 | Magne-Drisch et al. | |
| 6,747,181 B1 * | 6/2004 | Bosman et al. | 585/259 |
| 7,105,711 B2 | 9/2006 | Merrill | |
| 2005/0203320 A1* | 9/2005 | Ryu | 585/261 |
| 2006/0173224 A1* | 8/2006 | Putman et al. | 585/258 |

FOREIGN PATENT DOCUMENTS

| | | |
|---|---|---|
| CN | 1087892 | 6/1994 |
| CN | 1280975 | 1/2001 |
| CN | 1298376 | 6/2001 |
| CN | 1852877 A | 10/2006 |
| CN | 101475438 | 7/2009 |
| CN | 101475439 A | 7/2009 |
| JP | 07-278021 | 10/1995 |
| JP | 2005-535705 | 11/2005 |

OTHER PUBLICATIONS

International Search Report from the Chinese Patent Office in International Application No. PCT/CN2009/001487 mailed Mar. 25, 2010.
International Search Report dated Mar. 25, 2010, regarding International Application No. PCT/CN2009/001486.
Copending U.S. Appl. No. 13/140,616, filed Jun. 17, 2011.
English language abstract of JP 07-278021, dated Oct. 14, 1995.
English language abstract of JP 2005-535705, dated Nov. 24, 2005.

* cited by examiner

*Primary Examiner* — In Suk Bullock
*Assistant Examiner* — Sharon Pregler
(74) *Attorney, Agent, or Firm* — Finnegan, Henderson, Farabow, Garrett & Dunner LLP

(57) ABSTRACT

The present invention discloses a process for the selective hydrogenation of phenylacetylene in the presence of styrene conducted in a combined bed, which process comprises under hydrogenation reaction conditions, passing a hydrocarbon fraction feedstock containing phenylacetylene and styrene through a combined bed reactor containing a catalyst A and a catalyst B to contact the feedstock with the catalyst A and the catalyst B in turn, wherein the catalyst A is a nickel-based catalyst, the catalyst B is at least one selected from the group consisting of palladium-based catalysts and copper-based catalysts, and a weight ratio of the catalyst A loaded to the catalyst B loaded is from 0.5:1 to 5:1.

9 Claims, No Drawings

METHOD FOR SELECTIVE HYDROGENATION OF PHENYLACETYLENE USING COMPOSITE BED IN THE PRESENCE OF STYRENE

CROSS REFERENCE OF RELATED APPLICATION

The present application claims the priority of Application No. CN200810044147.5 filed on Dec. 18, 2008, which is incorporated herein by reference in its entirety and for all purposes.

TECHNICAL FIELD

The present invention relates to a process for the selective hydrogenation of phenylacetylene in the presence of styrene conducted in a combined bed, in particular to a process for removing phenylacetylene from a phenylacetylene-containing $C_8$ hydrocarbon fraction feedstock.

BACKGROUND ART

Styrene (ST) is an important monomer for producing polystyrene (PS), ABS resin, styrene-butadiene rubber, etc., and it is mainly produced by a process of dehydrogenating ethylbenzene. In recent years, along with the development and scale-up of ethylene industry, the technology of recovering styrene from pyrolysis gasoline draws more and more attention.

Pyrolysis gasoline is a by-product of ethylene industry, of which output is about 60 to 70% of ethylene output. $C_8$ fraction of pyrolysis gasoline is rich in styrene and mixed xylenes. An ethylene plant in 1000 kt/a scale can produce 24 to 42 kt/a of styrene, and at the same time mixed xylenes can be recovered. The production cost of styrene recovered from pyrolysis gasoline is about ½ of that of styrene produced by a process of dehydrogenating ethylbenzene.

The process for recovering styrene from pyrolysis gasoline that is widely regarded as being feasible at present is an extraction-distillation process. However, phenylacetylene (PA) and styrene are similar in chemical structure, and they also have similar interaction with an extraction-distillation solvent, so that it is impossible to achieve an effective separation of styrene from PA by the extraction-distillation. The presence of PA will not only increase the consumption of catalyst during anionic polymerization of styrene and affect chain length and polymerization rate, but also lead to worsen properties of polystyrene, e.g., off-color, degradation, odor-releasing and the like. Therefore, it is necessary to remove phenylacetylene from a styrene stream, while the loss of styrene should be as low as possible. Accordingly, the development of a high selectivity catalyst for the selective hydrogenation of phenylacetylene and of a relevant process becomes a key of the technology of recovering styrene from pyrolysis gasoline.

Patent application CN1852877A discloses a process for the reduction of phenylacetylene impurity in the presence of styrene monomer. A styrene monomer stream containing a minor amount of phenylacetylene is supplied to a hydrogenation reactor, and a hydrogenation gas comprising hydrogen is also supplied to the hydrogenation reactor. The styrene monomer stream and the hydrogen are brought into contact with a catalyst bed containing a catalyst comprising a reduced copper compound on a θ-alumina support. The hydrogenation reactor is operated at a temperature of at least 60° C. and a pressure of at least 30 psig to hydrogenate phenylacetylene to styrene. The hydrogenation gas comprises a mixture of nitrogen and hydrogen. This technique is featured with a relatively high reaction temperature, a low hydrogenation rate of phenylacetylene (about 70%), a short lifetime of catalyst, and a high loss of styrene (about 3%).

Patent application CN1087892A discloses a process and apparatus for purifying styrene monomer in a styrene stream by hydrogenation, wherein a diluent such as nitrogen is used to dilute hydrogen, the hydrogen is supplied by a vent gas from the dehydrogenation of ethylbenzene, and phenylacetylene impurity is hydrogenated to styrene by the aid of a multi-stage catalyst bed reactor. This patent is only directed to a process for the selective removal of phenylacetylene from a styrene stream containing phenylacetylene at a low concentration such as 300 ppm. On the other hand, the catalyst used exhibits a low hydrogenation rate of phenylacetylene (about 95%), and the loss of styrene is about 0.2%.

Thus, there is still need for a process to selectively hydrogenate phenylacetylene with a high selectivity useful in the technology for recovering styrene from pyrolysis gasoline.

SUMMARY OF THE INVENTION

In order to overcome the problems that the removal rate of phenylacetylene is low and that the loss of styrene is high, suffered by the existing techniques for removing phenylacetylene from a styrene stream by hydrogenation, the inventors have made diligently studies. As a result, the inventors have found that by using a combination of a nickel-based catalyst with a palladium-based and/or copper-based catalyst as hydrogenation catalyst, phenylacetylene in a styrene stream can be effectively removed and, at the same time, the loss of styrene is very low. On this basis, the present invention has been made.

Thus, an object of the present invention is to provide a novel process for the selective hydrogenation of phenylacetylene in the presence of styrene conducted in a combined catalyst bed. Said process has advantages that the removal rate of phenylacetylene is high and that the loss of styrene is low.

DESCRIPTION OF THE PREFERRED EMBODIMENTS

In an embodiment, the present invention relates to a process for the selective hydrogenation of phenylacetylene in the presence of styrene conducted in a combined bed, which process comprises under hydrogenation reaction conditions, passing a hydrocarbon fraction feedstock containing phenylacetylene and styrene through a combined bed reactor containing a catalyst A and a catalyst B to contact the feedstock with the catalyst A and the catalyst B in turn, wherein the catalyst A is a nickel-based catalyst, the catalyst B is at least one selected from the group consisting of palladium-based catalysts and copper-based catalysts, and a weight ratio of the catalyst A to the catalyst B is from 0.5:1 to 5:1.

In the process of the invention, the catalyst A is a nickel-based catalyst. The support of the catalyst A is at least one selected from the group consisting of silica, magnesia, alumina and molecular sieves, and preferably at least one of silica and alumina. The catalyst A has a nickel content of from 8 to 50 wt %, and preferably from 10 to 40 wt %, based on the support. In an embodiment, the catalyst A may be prepared by a process comprising the steps of: adding slowly an amount of a water-soluble nickel salt, e.g., nickel nitrate, into an aqueous diluted acid (e.g., nitric acid) solution and stirring to dissolve the nickel salt; then impregnating an amount of a support, e.g., alumina, with the resulting solution for, for example, more than 8 hours; and then drying and calcining, to obtain the desired nickel-based catalyst A.

In the process of the invention, the catalyst B is at least one selected from the group consisting of palladium-based catalysts and copper-based catalysts, and preferably a palladium-based catalyst. The support of the palladium-based catalysts and the copper-based catalysts is at least one selected from the group consisting of silica, magnesia, alumina and molecular sieves, and preferably at least one of silica and alumina. The palladium-based catalysts have a palladium content of from 0.1 to 5 wt %, and preferably from 0.2 to 3 wt %, based on the support. The copper-based catalysts have a copper content of from 10 to 60 wt %, and preferably from 12 to 40 wt %, based on the support. In an embodiment, a palladium-based catalyst as the catalyst B may be prepared by a process comprising the steps of pre-impregnating an amount of a support, e.g., alumina, with deionized water, and then filtering off the water; dissolving an amount of a water-soluble palladium salt, e.g., palladium nitrate, in water, and adjusting the solution with nitric acid to a pH value of about 3 to about 6; after suitably heating the solution, impregnating the water-filtered-off support with the solution; drying the impregnated support and calcining it in air, to obtain the palladium-based catalyst. A copper-based catalyst can be similarly prepared.

In a preferred embodiment, the present process is operated under the following conditions: a reactor inlet temperature of from 15 to 100° C., and preferably from 25 to 60° C.; a WHSV of from 0.01 to 100 $h^{-1}$, and preferably from 0.1 to 20 $h^{-1}$; a hydrogen/phenylacetylene molar ratio of from 1:1 to 30:1, and preferably from 1:1 to 10:1; and a reaction pressure of from −0.08 to 5.0 MPa (gauge, the same below), and preferably from 0.1 to 3.0 MPa.

The process of the invention can be used for removing phenylacetylene from a styrene-containing stream. There is not a specific limitation to the feedstock used in the process of the invention, as long as it contains styrene and phenylacetylene. The feedstock used in the process of the invention may be a $C_8$ fraction recovered from pyrolysis gasoline. Such a fraction may contain 20 to 60 wt % of styrene and 0.03 to 2 wt % of phenylacetylene.

It is well known that the hydrogenation reaction of phenylacetylene is a typical tandem reaction. Phenylacetylene is firstly hydrogenated to form styrene, and then the styrene may be further hydrogenated to form ethylbenzene. Ethylbenzene has an added value far lower than that of styrene, and thus the hydrogenation of styrene is undesired. Meanwhile, the presence of phenylacetylene is disadvantageous to subsequent separation, and affects the reaction of styrene, so that it is desired to remove phenylacetylene as much as possible. Therefore, furthest converting phenylacetylene whilst furthest avoiding the loss of styrene by hydrogenation is crucial for the technology of recovering styrene. After a lot of studies, we have discovered that, in the process of hydrogenating phenylacetylene with a nickel-, palladium-, or copper-based catalyst, the reaction activation energy of the step of hydrogenating phenylacetylene to produce styrene is lower than that of the step of hydrogenating styrene to produce ethylbenzene, so that all the palladium-based catalyst, the copper-based catalyst and the nickel-based catalyst have a relatively good selectivity for the hydrogenation of phenylacetylene. After further studies, the inventors have discovered that the nickel-based catalyst begins to exhibit catalytic activity at a lower temperature in the hydrogenation of phenylacetylene, while the palladium- or copper-based catalyst begins to exhibit catalytic activity at a higher temperature in comparison with the nickel-based catalyst. It is well known that the hydrogenation reaction is a typical exothermal reaction. For a conventional adiabatic hydrogenation reaction, as the hydrogenation reaction proceeds, the temperature of the catalyst bed will rise. If the concentration of phenylacetylene in the feedstock is about 1.5 wt %, the adiabatic temperature rise will be more than 20° C. Clearly, if a single catalyst is used, it is difficult for the catalyst to exhibit constantly a good catalytic activity over a relatively large temperature range. In the process of the invention, the inventors make the best of the characteristics of the nickel-, palladium- and copper-based catalysts in the hydrogenation reaction, and a combined catalyst bed, in which a nickel-based catalyst is located upstream and a palladium-based catalyst and/or a copper-based catalyst is/are located downstream, is utilized to achieve a good catalytic activity over a relatively large temperature range. In this way, not only the almost complete hydrogenation of phenylacetylene in the feedstock is ensured, but also the loss of styrene is furthest reduced. Furthermore, the process of the invention may be operated under a reduce pressure.

In an embodiment of the present invention, a $C_8$ fraction feedstock containing 20 to 60 wt % of styrene and 0.03 to 2 wt % of phenylacetylene is passed through a catalyst bed comprising the catalyst A and the catalyst B, to contact the feedstock with the catalyst A and the catalyst B in turn, wherein the catalyst A is a nickel-based catalyst comprising alumina as support and nickel in an amount of from 10 to 40 wt % based on the support, the catalyst B is a palladium-based catalyst comprising alumina as support and palladium in an amount of from 0.2 to 3 wt % based on the support, and a weight ratio of the catalyst A loaded to the catalyst B loaded is from 0.5:1 to 5:1, and wherein a reactor inlet temperature is from 25 to 60° C., a WHSV is from 0.1 to 20 $h^{-1}$, a hydrogen/phenylacetylene molar ratio is from 1:1 to 20:1, and a reaction pressure is from 0.1 to 3.0 MPa. Under such conditions, the hydrogenation rate of phenylacetylene may be up to 100%, while the loss of styrene may be almost zero, and even the situation where the amount of styrene is increased (or the loss of styrene is negative) due to the hydrogenation of phenylacetylene to styrene may occur.

EXAMPLES

The following examples are given for further illustrating the invention, but do not make limitation to the invention in any way.

General Procedures for Preparing the Catalysts

The nickel-based catalysts used in the following examples were prepared as follows:

An amount of nickel nitrate or nickel carbonate was added slowly into an aqueous solution of nitric acid having a pH value of 4 to 6, and the mixture was stirred to dissolve the nickel salt. Then an amount of a support, e.g., alumina, was impregnated with the resulting solution for more than 8 hours. The impregnated support was dried at 100 to 130° C., and then calcined at 500° C. for 4 hrs, to obtain the desired nickel-based catalyst.

The copper-based catalysts used in the following examples were prepared as follows:

An amount of copper nitrate or copper carbonate was dissolved in water to prepare an impregnation solution. An amount of a support, e.g., alumina or silica, was impregnated in the solution for 24 hrs. The impregnated support was dried at room temperature under vacuum for 8 to 12 hrs and further at 100 to 130° C. for 8 to 12 hrs, and then calcined at 350 to 450° C. for 4 to 8 hrs, to obtain the desired copper-based catalyst.

The palladium-based catalysts used in the following examples were prepared as follows:

An amount of a support, e.g., alumina, was pre-impregnated with deionized water, and then the water was filtered off. An amount of palladium nitrate was dissolved in water, and the solution was adjusted with nitric acid to a pH value of about 3 to about 6. The solution was heated to 60 to 80° C., and the water-filtered-off support was impregnated with the solution. The impregnated support was dried at 110 to 130° C. for 4 to 8 hrs, and then calcined in air at 300 to 450° C. for 4 to 8 hrs, to obtain the desired palladium-based catalyst.

Example 1

By using θ-alumina as support, nickel catalyst A having a nickel loading amount of 15 wt % and palladium catalyst B having a palladium loading amount of 0.8 wt % were prepared through the above-described processes. The catalyst A and the catalyst B were loaded in succession in a fixed bed adiabatic reactor, with a weight ratio of the catalyst A loaded to the catalyst B loaded being 1:1. Both the catalyst A and the catalyst B had been reduced with hydrogen at 300° C. for 4 hrs prior to use. Under the following conditions: a reactor inlet temperature of 40° C., a WHSV of 2 $hr^{-1}$, a hydrogen/phenylacetylene molar ratio of 3:1, and a reaction pressure of 0.2 MPa, a $C_8$ fraction feedstock containing 45 wt % of styrene, 42.85 wt % of xylenes, 12 wt % of ethyl benzene, and 0.15 wt % of phenylacetylene was passed through the reactor to contact in turn with the catalyst A and the catalyst B contained in the reactor. By analyzing the effluent from the reactor, it was found that the loss of styrene was 0.05 wt %, and the content of phenylacetylene was 1 ppmw.

Example 2

By using θ-alumina as support, nickel catalyst A having a nickel loading amount of 45 wt % and palladium catalyst B having a palladium loading amount of 0.2 wt % were prepared through the above-described processes. The catalyst A and the catalyst B were loaded in succession in a fixed bed adiabatic reactor, with a weight ratio of the catalyst A loaded to the catalyst B loaded being 3:1. Both the catalyst A and the catalyst B had been reduced with hydrogen at 300° C. for 4 hrs prior to use. Under the following conditions: a reactor inlet temperature of 35° C., a WHSV of 0.2 $hr^{-1}$, a hydrogen/phenylacetylene molar ratio of 15:1, and a reaction pressure of 3.5 MPa, a $C_8$ fraction feedstock containing 38 wt % of styrene, 15 wt % of ethyl benzene, 0.3 wt % of phenylacetylene, and the balance amount of xylenes was passed through the reactor to contact in turn with the catalyst A and the catalyst B contained in the reactor. By analyzing the effluent from the reactor, it was found that the loss of styrene was −0.1 wt %, and phenylacetylene was undetectable.

Example 3

By using γ-alumina as support, nickel catalyst A having a nickel loading amount of 20 wt % and palladium catalyst B having a palladium loading amount of 1.5 wt % were prepared through the above-described processes. The catalyst A and the catalyst B were loaded in succession in a fixed bed adiabatic reactor, with a weight ratio of the catalyst A loaded to the catalyst B loaded being 2:1. Both the catalyst A and the catalyst B had been reduced with hydrogen at 300° C. for 4 hrs prior to use. Under the following conditions: a reactor inlet temperature of 70° C., a WHSV of 30 $hr^{-1}$, a hydrogen/phenylacetylene molar ratio of 10:1, and a reaction pressure of −0.05 MPa, a $C_8$ fraction feedstock containing 35 wt % of styrene, 18 wt % of ethyl benzene, 0.08 wt % of phenylacetylene, and the balance amount of xylenes was passed through the reactor to contact in turn with the catalyst A and the catalyst B contained in the reactor. By analyzing the effluent from the reactor, it was found that the loss of styrene was 0.2 wt %, and the content of phenylacetylene was 10 ppmw.

Example 4

By using ZSM-5 molecular sieve as support, nickel catalyst A having a nickel loading amount of 30 wt % and palladium catalyst B having a palladium loading amount of 3 wt % were prepared through the above-described processes. The catalyst A and the catalyst B were loaded in succession in a fixed bed adiabatic reactor, with a weight ratio of the catalyst A loaded to the catalyst B loaded being 1.5:1. Both the catalyst A and the catalyst B had been reduced with hydrogen at 300° C. for 4 hrs prior to use. Under the following conditions: a reactor inlet temperature of 45° C., a WHSV of 10 $hr^{-1}$, a hydrogen/phenylacetylene molar ratio of 20:1, and a reaction pressure of 2.5 MPa, a $C_8$ fraction feedstock containing 30 wt % of styrene, 8 wt % of ethyl benzene, 1.2 wt % of phenylacetylene, and the balance amount of xylenes was passed through the reactor to contact in turn with the catalyst A and the catalyst B contained in the reactor. By analyzing the effluent from the reactor, it was found that the loss of styrene was −0.7 wt %, and phenylacetylene was undetectable.

Example 5

By using a 1:1 by weight mixture of γ-alumina and a-alumina as support, nickel catalyst A having a nickel loading amount of 10 wt % was prepared through the above-described process. By using ZSM-5 molecular sieve as support, copper catalyst B having a copper loading amount of 20 wt % was prepared through the above-described process. The catalyst A and the catalyst B were loaded in succession in a fixed bed adiabatic reactor, with a weight ratio of the catalyst A loaded to the catalyst B loaded being 0.5:1. Both the catalyst A and the catalyst B had been reduced with hydrogen at 300° C. for 4 hrs prior to use. Under the following conditions: a reactor inlet temperature of 30° C., a WHSV of 3 $hr^{-1}$, a hydrogen/phenylacetylene molar ratio of 6:1, and a reaction pressure of 2.0 MPa, a $C_8$ fraction feedstock containing 55 wt % of styrene, 3 wt % of ethyl benzene, 2 wt % of phenylacetylene, and the balance amount of xylenes was passed through the reactor to contact in turn with the catalyst A and the catalyst B contained in the reactor. By analyzing the effluent from the reactor, it was found that the loss of styrene was −1.5 wt %, and phenylacetylene was undetectable.

Example 6

By using γ-alumina as support, nickel catalyst A having a nickel loading amount of 20 wt % and copper catalyst B having a copper loading amount of 50 wt % were prepared through the above-described processes. The catalyst A and the catalyst B were loaded in succession in a fixed bed adiabatic reactor, with a weight ratio of the catalyst A loaded to the catalyst B loaded being 5:1. Both the catalyst A and the catalyst B had been reduced with hydrogen at 300° C. for 4 hrs prior to use. Under the following conditions: a reactor inlet temperature of 80° C., a WHSV of 60 $hr^{-1}$, a hydrogen/phenylacetylene molar ratio of 10:1, and a reaction pressure of 0.5 MPa, a $C_8$ fraction feedstock containing 30 wt % of styrene, 8 wt % of ethyl benzene, 0.8 wt % of phenylacetylene, and the balance amount of xylenes was passed through the reactor to contact in turn with the catalyst A and the catalyst B contained in the reactor. By analyzing the effluent from the reactor, it was found that the loss of styrene was 0.2 wt %, and the content of phenylacetylene was 1 ppmw.

Comparative Example 1

This experiment was carried out according to the procedure described in Example 1, except that a single catalyst bed of the catalyst B was used to replace for the combined bed of the catalyst A and the catalyst B. By analyzing the effluent from the reactor, it was found that the loss of styrene was 3 wt %, and the content of phenylacetylene was 10 ppmw.

Comparative Example 2

This experiment was carried out according to the procedure described in Example 5, except that a single catalyst bed of the catalyst B was used to replace for the combined bed of the catalyst A and the catalyst B. By analyzing the effluent from the reactor, it was found that the loss of styrene was 5 wt %, and the content of phenylacetylene was 20 ppmw.

Comparative Example 3

This experiment was carried out according to the procedure described in Example 5, except that a single catalyst bed of the catalyst A was used to replace for the combined bed of the catalyst A and the catalyst B. By analyzing the effluent from the reactor, it was found that the loss of styrene was 4 wt %, and the content of phenylacetylene was 18 ppmw.

The patents, patent applications and testing methods cited in the specification are incorporated herein by reference.

While the invention has been described with reference to exemplary embodiments, it will be understood by those skilled in the art that various changes and modifications may be made without departing from the spirit and scope of the invention. Therefore, the invention is not limited to the particular embodiments disclosed as the best mode contemplated for carrying out this invention, but the invention will include all embodiments falling within the scope of the appended claims.

What is claimed is:

1. A process for the selective hydrogenation of phenylacetylene in the presence of styrene conducted in a combined bed, which process comprises under hydrogenation reaction conditions, passing a hydrocarbon fraction feedstock containing phenylacetylene and styrene through a combined bed reactor containing a catalyst A and a catalyst B, wherein the hydrocarbon fraction feedstock contacts with the catalyst A first and then the catalyst B, wherein the catalyst A is a nickel-based catalyst, the catalyst B is at least one selected from the group consisting of palladium-based catalysts and copper-based catalysts, and a weight ratio of the catalyst A loaded to the catalyst B loaded is from 0.5:1 to 5:1.

2. The process of claim 1, wherein the hydrogenation reaction conditions include: a reactor inlet temperature of from 15 to 100° C., a WHSV of from 0.01 to 100 $h^{-1}$, a hydrogen/phenylacetylene molar ratio of from 1:1 to 30:1, and a reaction pressure of from −0.08 to 5.0 MPa.

3. The process of claim 1, wherein the catalyst A comprises at least one selected from the group consisting of silica, magnesia, alumina and molecular sieves as support, and has a nickel content of from 8 to 50 wt % based on the support.

4. The process of claim 3, wherein the catalyst A comprises silica and/or alumina as support, and has a nickel content of from 10 to 40 wt % based on the support.

5. The process of claim 1, wherein the catalyst B comprises at least one selected from the group consisting of silica, magnesia, alumina and molecular sieves as support, the palladium-based catalyst as catalyst B has a palladium content of from 0.1 to 5 wt % based on the support, and the copper-based catalyst as catalyst B has a copper content of from 10 to 60 wt % based on the support.

6. The process of claim 1, wherein the catalyst B is a palladium-based catalyst, which comprises silica and/or alumina as support, and has a palladium content of from 0.2 to 3 wt % based on the support.

7. The process of claim 1, wherein the hydrogenation reaction conditions include: a reactor inlet temperature of from 25 to 60° C., a WHSV of from 0.1 to 20 $h^{-1}$, a hydrogen/phenylacetylene molar ratio of from 1:1 to 20:1, and a reaction pressure of from 0.1 to 3.0 MPa.

8. The process of claim 1, wherein the phenylacetylene and styrene-containing hydrocarbon fraction feedstock contains 20 to 60 wt % of styrene and 0.03 to 2 wt % of phenylacetylene.

9. The process of claim 1, wherein the phenylacetylene and styrene-containing hydrocarbon fraction feedstock is a $C_8$ fraction recovered from pyrolysis gasoline.

* * * * *